(12) United States Patent
Kim

(10) Patent No.: US 12,690,823 B2
(45) Date of Patent: Jul. 28, 2026

(54) PERSONALIZED ALARM PROVISION SYSTEM USING BIOMETRIC INFORMATION AND MOTION INFORMATION ON BASIS OF DOPPLER SIGNAL

(71) Applicant: JCF TECHNOLOGY INC., Seoul (KR)

(72) Inventor: Jin Myung Kim, Bucheon-si (KR)

(73) Assignee: JCF TECHNOLOGY INC., Seoul (KR)

( * ) Notice: Subject to any disclaimer, the term of this patent is extended or adjusted under 35 U.S.C. 154(b) by 0 days.

(21) Appl. No.: 19/298,242

(22) Filed: Aug. 13, 2025

(65) Prior Publication Data

US 2025/0366797 A1 Dec. 4, 2025

Related U.S. Application Data

(63) Continuation of application No. PCT/KR2023/020352, filed on Dec. 11, 2023.

(30) Foreign Application Priority Data

Dec. 11, 2023 (KR) ........................ 10-2023-0178897

(51) Int. Cl.
A61B 5/00 (2006.01)
A61B 5/0205 (2006.01)
(Continued)

(52) U.S. Cl.
CPC ............ *A61B 5/746* (2013.01); *A61B 5/0205* (2013.01); *A61B 5/05* (2013.01); *G01S 13/62* (2013.01);
(Continued)

(58) Field of Classification Search
CPC ... H04N 21/44224; H04N 2005/91328; H04N 2005/91364; H04N 21/4131;
(Continued)

(56) References Cited

U.S. PATENT DOCUMENTS 5,903,217 A * 5/1999 Stanczak ................. G01S 7/003
340/552
2007/0296578 A1 * 12/2007 Duff ........................ G01S 13/56
340/567
(Continued)

FOREIGN PATENT DOCUMENTS

JP 2001344675 A 12/2001
JP 2003006770 A 1/2003
(Continued)

*Primary Examiner* — Daniel Previl
(74) *Attorney, Agent, or Firm* — NKL LAW; Jae Youn Kim

(57) ABSTRACT
The present invention relates to a personalized alarm provision system using biometric information and motion information on the basis of a Doppler signal, comprising: an acquisition device that emits a radar signal to a subject and analyzes a Doppler signal generated through a reflected wave acquired by reflecting the emitted radar signal to acquire bio-signal or motion signal information of the subject from the Doppler signal; a server; and a guardian terminal.

6 Claims, 3 Drawing Sheets

(51) Int. Cl.

| | |
|---|---|
| *A61B 5/05* | (2021.01) |
| *G01S 13/62* | (2006.01) |
| *G01S 13/88* | (2006.01) |
| *A61B 5/021* | (2006.01) |
| *A61B 5/08* | (2006.01) |
| *A61B 5/11* | (2006.01) |

(52) U.S. Cl.
CPC ............. *G01S 13/886* (2013.01); *A61B 5/021* (2013.01); *A61B 5/0816* (2013.01); *A61B 5/1118* (2013.01); *A61B 5/4809* (2013.01)

(58) Field of Classification Search
CPC ......... H04N 21/42201; H04N 21/4532; H04N 21/47; H04N 5/782; H04N 5/913; H04N 21/4318; H04N 21/44008; H04N 21/4668; H04N 21/475; H04N 7/163; G05B 15/02; G06F 3/048; G06F 16/9538; G06F 16/9577; G06F 16/951; G06F 16/9536; G06F 17/00; G06N 20/00; G06N 5/025; G06N 7/01; G06Q 30/02; G06Q 30/0248; G06Q 30/0255; G06Q 30/0267; G06Q 30/0269; G06Q 30/0273; G06Q 30/0201; G06Q 30/0251; G06Q 30/0282; G06Q 99/00; G06Q 10/0631; G06Q 10/103; G06Q 10/40; G06Q 50/10; G06Q 50/22; G06Q 50/40; G06Q 90/00; A61B 5/1118; A61B 2503/10; A61B 5/11; A61B 5/1123; A61B 5/4866; A61B 2562/0219; A61B 5/0006; A61B 5/0008; A61B 5/0013; A61B 5/002; A61B 5/0022; A61B 5/0077; A61B 5/01; A61B 5/0205; A61B 5/02055; A61B 5/021; A61B 5/0261; A61B 5/05; A61B 5/053; A61B 5/0816; A61B 5/1112; A61B 5/1113; A61B 5/1116; A61B 5/1117; A61B 5/165; A61B 5/318; A61B 5/369; A61B 5/384; A61B 5/389; A61B 5/395; A61B 5/4806; A61B 5/4809; A61B 5/4812; A61B 5/486; A61B 5/6803; A61B 5/6806; A61B 5/6807; A61B 5/681; A61B 5/6824; A61B 5/6826; A61B 5/6891; A61B 5/7264; A61B 5/742; A61B 5/746; A61B 7/00; A61B 7/04; A61B 7/045; A61B 8/00; A61B 8/06; A61B 8/0808; A61B 8/4427; A61B 8/488; A61B 8/565; G16H 20/30; G16H 20/70; G16H 40/67; G16H 10/20; G16H 10/60; G16H 15/00; G16H 20/10; G16H 20/13; G16H 20/60; G16H 40/63; G16H 50/20; G16H 50/30; G16H 50/70; G16H 70/40; G16H 80/00; A63B 24/0062; A63B 24/00; G01S 19/05; G01S 19/19; G01S 13/56; G01S 13/62; G01S 13/886; G09B 19/0038; G09B 5/00; A43B 3/42; A43B 3/46; A43B 3/48; A47J 36/32; A47J 36/321; A47J 44/00; B25J 11/0045; B25J 13/06; B82Y 10/00; G06V 40/103; G07F 17/32; G07F 17/3206; G07F 17/3216; G07F 17/3239; G08B 21/02; G08B 21/04; G08B 21/0423; G08B 21/0446; G08B 21/0453; G08B 21/0461; G08B 21/0476; G08B 21/0484; G08B 21/0492; G08B 21/18; G08B 25/016; G16Z 99/00; G21K 1/093; H04B 10/90; H04L 9/0852; H04M 2250/12; H04M 3/5116; H04W 84/18
USPC ......... 340/573.1, 554, 545.3, 552, 521, 540, 340/541, 545, 572.1, 572.2, 572.4, 573.7, 340/567
See application file for complete search history.

(56) References Cited

U.S. PATENT DOCUMENTS

| | | | | |
|---|---|---|---|---|
| 2014/0019157 A1* | 1/2014 | Nudd | ..................... | G16H 40/67 |
| | | | | 705/2 |
| 2014/0142403 A1* | 5/2014 | Brumback | ........... | A61B 5/7475 |
| | | | | 600/479 |
| 2018/0228473 A1* | 8/2018 | Cho | ...................... | A61B 8/469 |
| 2019/0064344 A1* | 2/2019 | Turner | ................... | G08B 21/02 |
| 2023/0200749 A1* | 6/2023 | Rahamim | ........... | A61B 5/0022 |
| | | | | 600/301 |

FOREIGN PATENT DOCUMENTS

| | | | |
|---|---|---|---|
| JP | 2012005745 A | 1/2012 |
| JP | 2015109991 A | 6/2015 |
| JP | 2019153295 A | 9/2019 |
| KR | 102060101 B1 | 12/2019 |
| KR | 20200113910 A | 10/2020 |
| KR | 102289031 B1 | 8/2021 |
| KR | 102347534 B1 | 1/2022 |

* cited by examiner

PERSONALIZED ALARM PROVISION SYSTEM USING BIOMETRIC INFORMATION AND MOTION INFORMATION ON BASIS OF DOPPLER SIGNAL

TECHNICAL FIELD

The present invention relates to a personalized alarm provision system that informs of a danger situation based on individual statistics on the basis of biometric information and motion signal information acquired using a Doppler signal.

BACKGROUND ART

Recently, the number of people in need of care or attention is increasing in the domestic society. The people in need of care or attention may be defined as people who need assistance when an emergency situation occurs or people who do not have a housemate, and for example, the elderly, the disabled, and single-person households may be included. According to a recent survey, the elderly population has exceeded 9 million, and the population of single-person households and registered disabled people has also exceeded 6.6 million and 2.6 million, respectively. In addition, the number of people who die alone due to absence of a housemate exceeds 20,000.

In addition, together with increase in the number of personal terminals and demands for personal health management, various solutions or applications that collect personal healthcare data and provide personalized health management contents using the personal healthcare data are emerging one after another recently. Wearable devices or installation-type devices are used to collect such individual healthcare data. When the wearable devices are used, pre-processing of measured data is not needed in many cases since healthcare data is acquired from the parts close to the body. However, in the case of the installation-type devices, since physical activity information of a user is measured from a distance, there is a problem in that the probability of mixing measured data with noise increases, and it is difficult to distinguish a subtle difference.

In addition, as existing danger notification services for elderly persons living alone are provided assuming generalized danger situations rather than personalized ones, there is a disadvantage incapable of providing personalized danger notification services.

DISCLOSURE OF INVENTION

Technical Problem

Therefore, the present invention has been made in view of the above problems, and it is an object of the present invention to provides a biometric signal and motion signal information acquisition device using a Doppler signal, which can accurately acquire biometric signal or motion signal information of a subject from the Doppler signal by emitting a radar signal to the subject and analyzing the Doppler signal generated through a reflected wave acquired as the emitted radar signal is reflected.

In addition, another object of the present invention is to provide a personalized danger situation alarm based on biometric information and motion information derived using a biometric signal and motion signal information acquisition device using a Doppler signal.

Technical Solution

To accomplish the above object, according to one aspect of the present invention, there is provided a biometric signal and motion signal information acquisition device using a Doppler signal, a server, and a guardian terminal.

The biometric signal and motion signal information acquisition device using a Doppler signal may include: a Doppler signal acquisition unit for emitting a radar signal to a subject, acquiring a reflected and returned radar signal to acquire a Doppler signal, and processing the Doppler signal to acquire a first phase Doppler signal and a second phase Doppler signal; a Doppler signal processing unit for processing the first phase Doppler signal and the second phase Doppler signal to acquire first signal information and second signal information, respectively; and a signal information output unit for acquiring the first signal information and the second signal information, and analyzing the first signal information and the second signal information using a preset algorithm to acquire biometric signal information and motion signal information.

The server may acquire life pattern information by statistically calculating a time of staying in each space of a household on the basis of the motion signal information and biometric signal information, and set living spaces and danger spaces on the basis of the life pattern information.

The server may acquire the life pattern information by statistically calculating the time of staying in each space on the basis of the motion signal information transmitted from the biometric signal and motion signal information acquisition device installed in each space of a household, set a space where the subject stays the longest as a first living space, and set a restroom or a bathroom as a first danger space.

The server may set an entrance as a second danger space, and set a space that is neither the first danger space nor the second danger space, where the subject stays for a shorter period of time than in the first living space, as a second living space.

The server may generate a first alarm signal when a time that the subject stays in the first danger space in a first time zone has passed $5n$ minutes in the case where the time that the subject stays in the first danger space in the first time zone is $n$ minutes on the basis of the life pattern information.

The server may generate a second alarm signal when a time that the subject stays in the second danger space has passed $10n$ minutes in the case where the time that the subject stays in the second danger space is $n$ minutes on the basis of the life pattern information.

The server may generate a third alarm signal when a ratio of the time that the subject stays in the first living space exceeds 8 times a ratio of a time that the subject is out of the first living space.

The server may generate a fourth alarm signal when an amount of activity of the subject decreases in a preset time zone.

When a moving speed of the subject in the motion signal is higher than a preset value or when an area of a movement subject exceeds a preset range, the server may determine that the amount of activity has occurred on the basis of the motion signal information.

The server may statistically derive maximum heart and respiration rates, minimum heart and respiration rates, and average heart rate and respiration rates in sleeping and non-sleeping states on the basis of the motion signal information and biometric signal information, determine a normal range of a heart rate and a respiratory rate of the subject in the sleeping and non-sleeping states on the basis of the statistical maximum heart and respiratory rates, minimum heart and respiratory rates, average heart and respiratory rates in the sleeping and non-sleeping states, and generate a fourth alarm signal when a heart rate and a respiratory rate exceeding the normal range are derived in the sleeping or non-sleeping state.

The personalized alarm provision system may further comprise an external terminal that transmits exercise information of the subject.

The server may receive an age, a gender, exercise information, drug information, and weight information of the subject from the guardian terminal, determine a first heart rate range according to the age of the subject in the non-sleeping state, then, determine a second heart rate corrected to be 5 to 10% higher than the first heart rate when the gender of the subject is female, and determine a third heart rate corrected to be 5 to 10% lower than the first heart rate when the gender of the subject is male, then, determine a fourth heart rate corrected to be 5 to 10% lower than the second heart rate and a fifth heart rate corrected to be 5 to 10% lower than the third heart rate when it is determined that the subject exercises more than a predetermined amount of exercise within a predetermined cycle on the basis of the exercise information received from the external terminal, then, determine a sixth heart rate correcting the fourth heart rate, and determine a seventh heart rate correcting the fifth heart rate on the basis of the drug information and weight information of the subject, and determine that an emergency situation has occurred, and generate a fifth alarm signal when the sixth heart rate and the seventh heart rate exceed a preset range.

Advantageous Effects

The personalized alarm provision system using biometric information and motion information based on a Doppler signal according to an embodiment of the present invention has an effect of accurately acquiring biometric signal or motion signal information of a subject from the Doppler signal by emitting a radar signal to the subject and analyzing the Doppler signal generated through a reflected wave acquired as the emitted radar signal is reflected.

The personalized alarm provision system using biometric information and motion information based on a Doppler signal of the present invention has an effect of notifying a guardian of a danger situation by determining a personal danger situation differently on the basis of life pattern information statistically calculated for each situation of an individual.

BEST MODE FOR CARRYING OUT THE INVENTION

Figure 1:
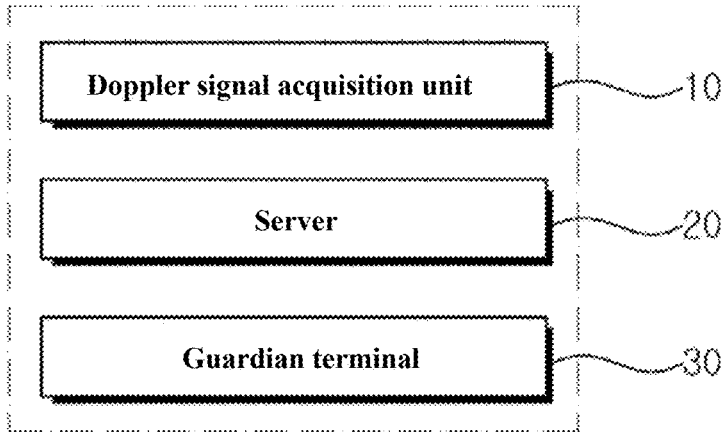
FIG. 1 is a block diagram showing a personalized alarm provision system using biometric information and motion information based on a Doppler signal according to an embodiment of the present invention.

Hereinafter, some embodiments of the present disclosure will be described in detail with reference to illustrative drawings. In adding reference numerals to components in each drawing, like components may have like reference numerals as much as possible although they are shown in different drawings. In addition, in describing the present embodiments, when it is determined that a detailed description of a related known configuration or function may obscure the gist of the present technical spirit, the detailed description may be omitted. When "comprise", "have", "configured of", and the like mentioned in the specification are used, other parts may be added as long as "only" is not used. When a component is expressed in a singular form, it may also include the plural, unless specifically stated otherwise.

In addition, in describing the components of the present disclosure, terms such as first, second, A, B, (a), and (b) may be used. These terms are used only to distinguish the components from other components, and the nature, sequence, order, or number of the components are not limited by the terms.

When two or more components are described as being "connected", "coupled", or "combined" in describing the positional relationship of components, although two or more components may be directly "connected", "coupled", or "combined", it should be understood that the two or more components are "connected", "coupled", or "combined" as other components are further "interposed". Here, other components may be included in one or more of two or more components "connected", "coupled", or "combined" with each other.

In describing the relationship of temporal flows related to the components, operation methods, manufacturing methods, and the like, for example, when a temporal precedence relationship or a flow precedence relationship is described as "after", "in succession to", "next", "before", or the like, non-successive cases may also be included unless "immediately" or "directly" is used.

Meanwhile, when a numerical value about a component or information corresponding thereto (e.g., levels, etc.) is mentioned, although there is no explicit description separately, the numerical value or information corresponding thereto may be interpreted as including a range of error that may occur due to various factors (e.g., processing factors, internal or external shocks, noise, and the like).

A personalized alarm provision system 100 using biometric information and motion information based on a Doppler signal according to an embodiment of the present invention may include a biometric signal and motion signal information acquisition device 10 using a Doppler signal, a server 20, and a guardian terminal 30.

Figure 2:
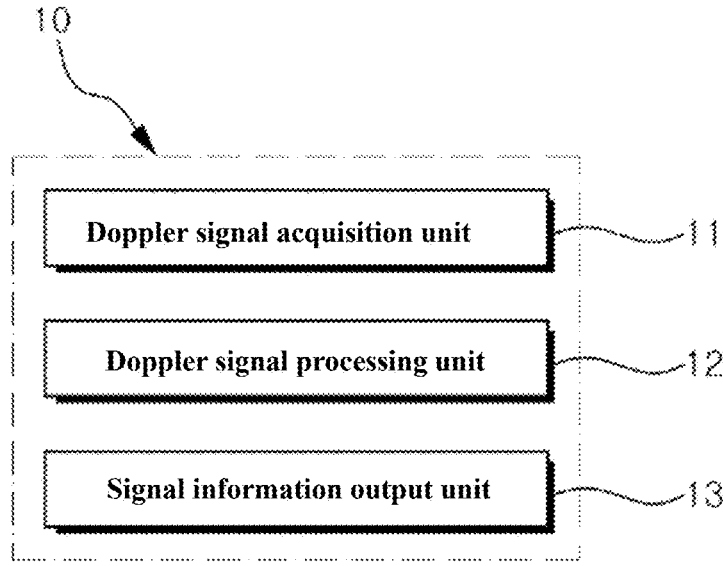
FIG. 2 is a block diagram showing a biometric signal and motion signal information acquisition device using a Doppler signal according to an embodiment of the present invention.
Figure 3:
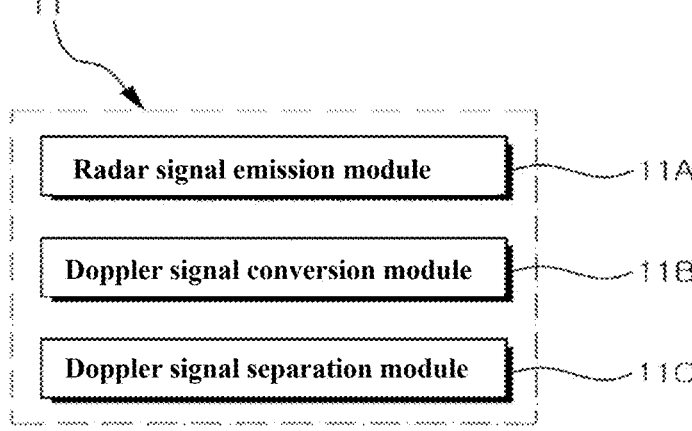
FIG. 3 is a block diagram showing the Doppler signal acquisition unit of FIG. 2.
Figure 4:
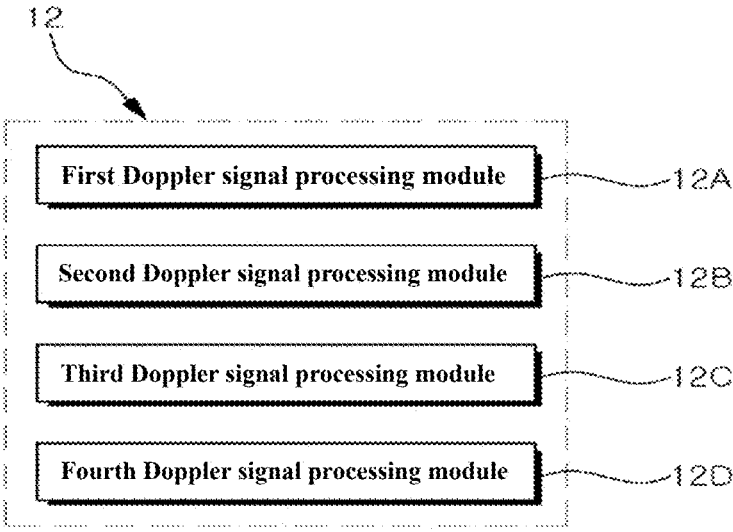
FIG. 4 is a block diagram showing the Doppler signal processing unit of FIG. 2.

1. A Biometric Signal and Motion Signal Information Acquisition Device 10 Using a Doppler Signal FIGS. 2 to 4 show an embodiment of a biometric signal and motion signal information acquisition device 10 using a Doppler signal according to the present invention. FIG. 2 is a block diagram showing a biometric signal and motion signal information acquisition device 10 using a Doppler signal according to an embodiment of the present invention, FIG. 3 is a block diagram showing the Doppler signal acquisition unit of FIG. 2, and FIG. 4 is a block diagram showing the Doppler signal processing unit of FIG. 2.

The biometric signal and motion signal information acquisition device 10 using a Doppler signal may be installed in a plurality of locations within a single household. Preferably, the biometric signal and motion signal information acquisition device 10 using a Doppler signal may be installed in a bedroom, living room, small room, restroom, entrance, and the like within a single household.

In addition, the biometric signal and motion signal information acquisition device 10 using a Doppler signal may be installed on the ceiling to acquire a wide range of biometric signal and motion signal information. In addition, in some cases, a plurality of devices 10 for acquiring biometric signal and motion signal information using a Doppler signal may be installed within a space. For example, the devices 10 for acquiring biometric signal and motion signal information using a Doppler signal may also be installed on the restroom ceiling and the restroom wall. When the devices are installed in this way, there is an advantage of detecting a fall accident more accurately.

Hereinafter, a biometric signal and motion signal information acquisition device using a Doppler signal of the present invention will be described in detail with reference to FIGS. 2 to 4.

The biometric signal and motion signal information acquisition device 10 using a Doppler signal according to an embodiment of the present invention is formed to emit a radar signal to a subject, acquire a Doppler signal, and perform a plurality of filtering and amplification processes on the acquired Doppler signal to acquire a biometric signal and a motion signal. To this end, the biometric signal and motion signal information acquisition device 10 using a Doppler signal according to an embodiment of the present invention may be formed to include a Doppler signal acquisition unit 11, a Doppler signal processing unit 12, and a signal information output unit 13 as shown in FIG. 2.

The Doppler signal acquisition unit 11 is formed to emit a radar signal to a subject, acquire the reflected and returned radar signal to acquire a Doppler signal, and process the Doppler signal to acquire a first phase Doppler signal and a second phase Doppler signal.

In the case of a radar signal, when there is a motion of a subject, a Doppler signal is generated. The Doppler signal acquisition unit 11 of the present invention may be formed to emit a radar signal to a subject by utilizing the characteristics of a Doppler radar and acquire a Doppler signal through a reflected and returned signal. To this end, the Doppler signal acquisition unit 11 according to an embodiment of the present invention may include a radar signal emission module 11A, a Doppler signal conversion module 11B, and a Doppler signal separation module 11C, as shown in FIG. 3.

The radar signal emission module 11A is formed to emit a radar signal to a subject, and the Doppler signal conversion module 11B is formed to acquire a radar signal reflected and returned from the subject to acquire a Doppler signal. In an embodiment of the present invention, a Doppler signal can be acquired using a 24 GHz radar signal.

The Doppler signal separation module 11C is formed to perform processing on the Doppler signal acquired from the Doppler signal conversion module 11B to acquire a first phase Doppler signal and a second phase Doppler signal.

Here, the first phase Doppler signal may be processed to have a phase difference of 90 degrees from the second phase Doppler signal.

The Doppler signal processing unit 12 according to an embodiment of the present invention is formed to process, when the Doppler signal acquisition unit 11 acquires a first phase Doppler signal and a second phase Doppler signal, the first phase Doppler signal and the second phase Doppler signal to acquire first signal information and second signal information, respectively. The first signal information and the second signal information may be acquired from the first phase Doppler signal and the second phase Doppler signal, respectively.

The first signal information and the second signal information acquired through the first phase Doppler signal may be defined as 1-1 signal information and 1-2 signal information, and the first signal information and the second signal information acquired through the second phase Doppler signal may be defined as 2-1 signal information and 2-2 signal information.

Here, the 1-1 signal information may be heart rate information, and the 2-1 signal information may be respiratory rate information.

In addition, the 1-2 signal may be a moving speed, and the 2-2 signal may be an area of a movement subject.

To this end, the Doppler signal processing unit 12 of the present invention may be formed to include a first Doppler signal processing module 12A, a second Doppler signal processing module 12B, and a third Doppler signal processing module 12C, as shown in FIG. 4. Hereinafter, although it is described that the Doppler signal processing unit 12 of the present invention uses three or more Doppler signal processing modules for convenience of explanation, the present invention is not limited thereto, and may operate using N Doppler signal processing modules set by a manager.

The first Doppler signal processing module 12A is formed to perform first filtering and first amplification on the first phase Doppler signal and the second phase Doppler signal to acquire a 1-1 phase Doppler processed signal and a 2-1 phase Doppler processed signal.

Figure 7:
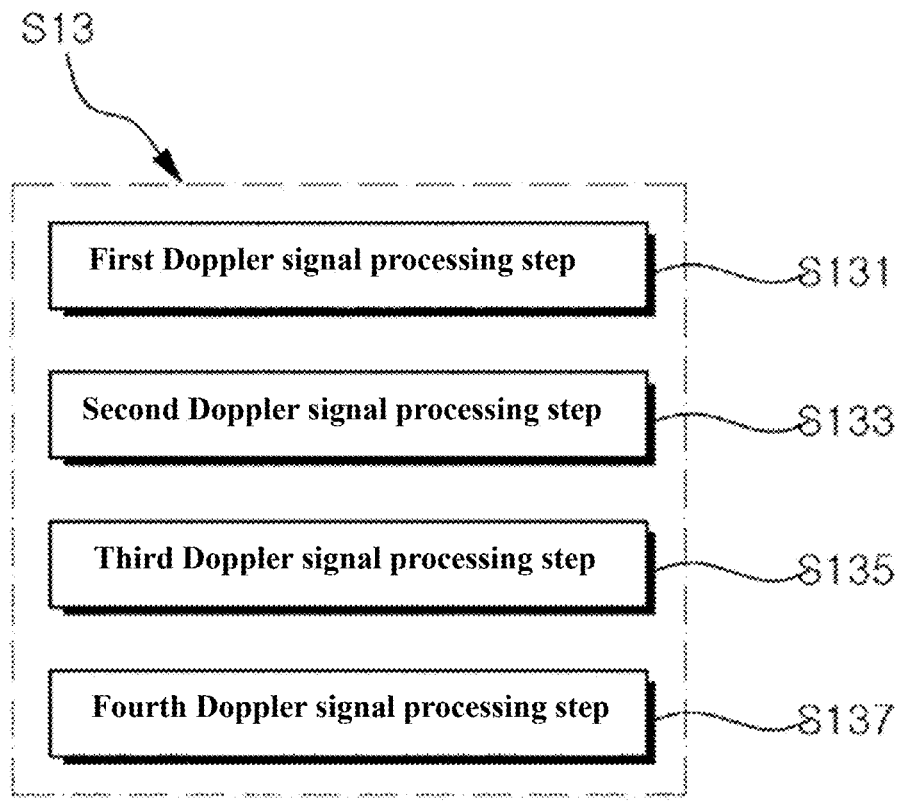
FIG. 7 is a flowchart illustrating step S13 of FIG. 5.

The first Doppler signal processing module 12A is formed to perform processing on the first phase Doppler signal and the second phase Doppler signal, and although it is described in the present invention that only the first Doppler signal processing module 12A performs processing on the first and second phase Doppler signals, the present invention is not necessarily limited thereto, and as shown in FIG. 7, a 1-1 Doppler signal processing module for processing the first phase Doppler signal and a 1-2 Doppler signal processing module for processing the second phase Doppler signal may be provided.

The first filtering performed in the first Doppler signal processing module 12A may be a process of performing low-pass filtering (LPF) by applying a filter of a frequency band set by the manager. In addition, the first amplification performed in the first Doppler signal processing module 12A may be a process of amplifying the input first and second phase Doppler signals as much as an amplification factor set by the manager. An active filter may be used as the first Doppler signal processing module 12A according to an embodiment of the present invention, and the active filter is a filter that performs amplification and filtering simultaneously by utilizing circuit characteristics.

When the 1-1 phase Doppler processed signal and the 2-1 phase Doppler processed signal are generated through the first filtering and the first amplification, the generated 1-1 phase Doppler processed signal and 2-1 phase Doppler processed signal are transmitted to the second Doppler signal processing module 12B and the third Doppler signal processing module 12C through a branch circuit. The second Doppler signal processing module 12B and the third Doppler signal processing module 12C are connected in parallel, and although both the second Doppler signal processing module 12B and the third Doppler signal processing module 12C process the 1-1 phase Doppler processed signal and the 2-1 phase Doppler processed signal, the two modules are formed to perform different processing.

Describing more specifically, the second Doppler signal processing module 12B and the third Doppler signal processing module 12C are connected to the first Doppler signal processing module 12A, and the second Doppler signal processing module 12B and the third Doppler signal processing module 12C may be connected to each other in a parallel structure.

This is since that in an embodiment of the present invention, the second Doppler signal processing module 12B and the third Doppler signal processing module 12C are formed to process a signal lower than a preset frequency or a signal higher than a preset reference frequency, respectively. In an embodiment of the present invention, the third Doppler signal processing module 12C may be formed to process, when the second Doppler signal processing module 12B is formed to process a signal lower than a preset frequency, a signal higher than the preset frequency. This simply means that different frequency bands are processed through different Doppler signal processing modules, and the second Doppler signal processing module 12B and the third Doppler signal processing module 12C may process opposite frequency bands.

In addition, as such a parallel structure is applied, the second Doppler signal processing module 12B and the third Doppler signal processing module 12C may have different amplification ratios in an embodiment of the present invention, and to this end, the second Doppler signal processing module 12B and the third Doppler signal processing module 12C may be formed to further connect an additional Doppler signal processing module. In the present invention, a fourth Doppler signal processing module 12D described below may be the additional Doppler signal processing module described above.

The second Doppler signal processing module 12B is formed to perform second filtering and second amplification on the 1-1 phase Doppler processed signal and the 2-1 phase Doppler processed signal to acquire the 1-1 signal information and the 2-1 signal information.

The second Doppler signal processing module 12B is formed to perform processing on the 1-1 phase Doppler processed signal and the 2-1 phase Doppler processed signal, and although it is described in the present invention that only the second Doppler signal processing module 12B performs processing on the 1-1 and 2-1 phase Doppler processed signals, the present invention is not necessarily limited thereto, and as shown in FIG. 7, a 2-1 Doppler signal processing module for processing the 1-1 phase Doppler signal and a 2-2 Doppler signal processing module for processing the 2-1 phase Doppler signal may be provided.

The second filtering performed in the second Doppler signal processing module 12B may be a process of removing DC components from the 1-1 phase Doppler processed signal and the 2-1 phase Doppler processed signal, and performing high-pass filtering (HPF) by applying a filter of a frequency band set by the manager.

In addition, the second amplification performed in the second Doppler signal processing module 12B may be a process of amplifying the input 1-1 phase Doppler processed signal and 2-2 phase Doppler processed signal as much as an amplification factor set by the manager. An active filter may be used as the second Doppler signal processing module 12B according to an embodiment of the present invention, and the active filter is a filter that performs amplification and filtering simultaneously by utilizing circuit characteristics.

The third Doppler signal processing module 12C is formed to acquire the 1-1 phase Doppler processed signal and the 2-1 phase Doppler processed signal, which are the same signals as those processed by the second Doppler signal processing module 12B, and perform third filtering and third amplification on the acquired 1-1 phase Doppler processed signal and 2-1 phase Doppler processed signal to acquire 1-2 signal information and 2-2 signal information.

The third Doppler signal processing module 12C is formed to perform processing on the 1-1 phase Doppler processed signal and the 2-1 phase Doppler processed signal, and although it is described in the present invention that only the third Doppler signal processing module 12C performs processing on the 1-1 and 2-1 phase Doppler processed signals, the present invention is not necessarily limited thereto, and as shown in FIG. 7, a 3-1 Doppler signal processing module for processing the 1-1 phase Doppler signal and a 3-2 Doppler signal processing module for processing the 2-1 phase Doppler signal may be provided.

The third filtering performed in the third Doppler signal processing module 12C may be a process of performing low-pass filtering (LPF) and high-pass filtering (HPF) by applying a filter of a frequency band range set by the manager. In addition, the third amplification performed in the third Doppler signal processing module 12C may be a process of amplifying the input 1-1 and 2-1 phase Doppler processed signals as much as an amplification factor set by the manager. An active filter may be used as the third Doppler signal processing module 12C according to an embodiment of the present invention, and the active filter is a filter that performs amplification and filtering simultaneously by utilizing circuit characteristics.

Meanwhile, in another embodiment of the present invention, a fourth Doppler signal processing module 12D may be further included as shown in FIG. 4. The fourth Doppler signal processing module 12D may be formed to perform processing on the processing result of the second Doppler signal processing module 12C. At this point, when the fourth Doppler signal processing module 12D exists, the first Doppler signal processing module 12A, the second Doppler signal processing module 12B, and the fourth Doppler signal processing module 12D may be connected in series. In addition, the signal output from the second Doppler signal processing module 12B may be a 1-2 phase Doppler processed signal and a 2-2 phase Doppler processed signal, rather than the 1-1 signal information and the 2-1 signal information.

The fourth Doppler signal processing module 12D is formed to perform, when the 1-2 phase Doppler processed signal and the 2-2 phase Doppler processed signal are acquired from the second Doppler signal processing module 12B, fourth filtering and fourth amplification on the 1-2 phase Doppler processed signal and the 2-2 phase Doppler processed signal to acquire the 1-1 signal information and the 2-1 signal information.

The fourth Doppler signal processing module 12D is formed to perform processing on the 1-2 phase Doppler processed signal and the 2-2 phase Doppler processed signal, and although it is described in the present invention that only the fourth Doppler signal processing module 12D performs processing on the 1-2 and 2-2 phase Doppler processed signals, the present invention is not necessarily limited thereto, and as shown in FIG. 7, a 4-1 Doppler signal processing module for processing the 1-2 phase Doppler signal and a 4-2 Doppler signal processing module for processing the 2-2 phase Doppler signal may be provided.

The fourth filtering performed in the fourth Doppler signal processing module 12D may be a process of applying low-pass filtering (LPF) to the 1-2 phase Doppler processed signal and the 2-2 phase Doppler processed signal by applying a filter of a frequency band range set by the manager, and the fourth amplification may be a process of amplifying the input 1-2 phase Doppler processed signal and 2-2 phase Doppler processed signal as much as an amplification factor set in advance by the manager.

An active filter may be used as the fourth Doppler signal processing module 12D according to an embodiment of the present invention, and the active filter is a filter that performs amplification and filtering simultaneously by utilizing circuit characteristics.

In addition, the fourth Doppler signal processing module 12D may be formed to apply a DC offset voltage set by the manager to a signal on which the third filtering and second amplification are performed.

In an embodiment of the present invention, the 1-1 signal information and the 2-1 signal information may be information including biological motion information, and the 1-2 signal information and the 2-2 signal information may be information including movement motion information.

Accordingly, the signal information output unit 13 according to an embodiment of the present invention is formed to acquire first signal information and second signal information, and analyze the first signal information and the second signal information using a preset algorithm to acquire biometric signal information and motion signal information.

The signal information output unit 13 of the present invention may acquire 1-1 signal information and 2-1 signal information as the first signal information, and 1-2 signal information and 2-2 signal information as the second signal information. That is, in the present invention, the first signal information may be defined to include biological motion information, and the second signal information may be defined to include movement motion information.

The signal information output unit 13 may be formed to apply the acquired biological motion information and movement motion information to a preset algorithm to acquire and output biometric signal information and motion signal information from each motion information. The biometric signal information and motion signal information acquired by the signal information output unit 13 may be transmitted to the communication unit 14.

The communication unit 14 may transmit the biometric signal information and motion signal information received from the signal information output unit 13 to the server 20 through wired or wireless communication.

Figure 5:
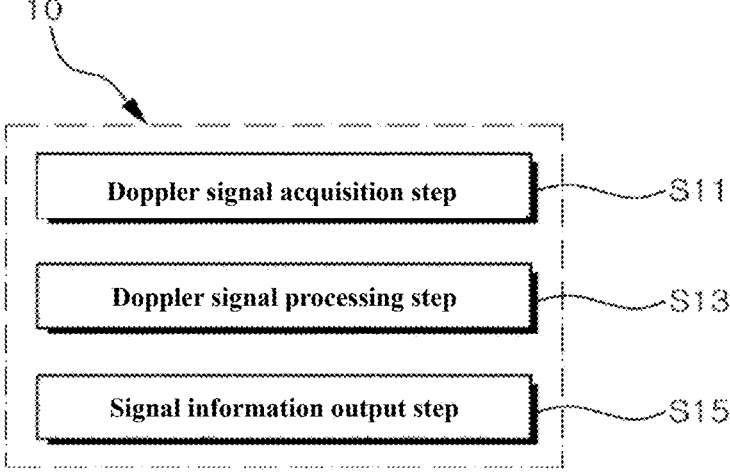
FIG. 5 is a flowchart illustrating a method of acquiring biometric signal and motion signal information using a Doppler signal according to an embodiment of the present invention.
Figure 6:
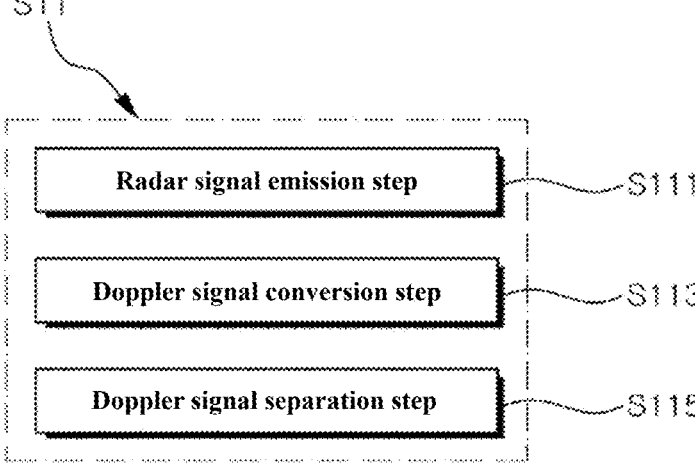
FIG. 6 is a flowchart illustrating step S11 of FIG. 5.

A method of Acquiring Biometric Signal and Motion Signal Information Using a Doppler Signal FIGS. 5 to 7 show an embodiment of a method of acquiring biometric signal and motion signal information using a Doppler signal according to the present invention. FIG. 5 is a flowchart illustrating a method of acquiring biometric signal and motion signal information using a Doppler signal according to an embodiment of the present invention, FIG. 6 is a flowchart illustrating step S11 of FIG. 5, and FIG. 7 is a flowchart illustrating step S13 of FIG. 5.

Hereinafter, a method of acquiring biometric signal and motion signal information using a Doppler signal according to the present invention will be described in detail with reference to FIGS. 5 to 7. In addition, although it is described with reference to FIG. 2 for convenience of explanation, the present invention is not limited thereto, and the devices, systems, terminals, and the like capable of performing various similar functions or operations may be used.

A method 10 of acquiring biometric signal and motion signal information using a Doppler signal according to an embodiment of the present invention is formed to acquire a Doppler signal after emitting a radar signal to a subject, and perform a plurality of filtering and amplification processes on the acquired Doppler signal to acquire a biometric signal and a motion signal. To this end, the method 10 of acquiring biometric signal and motion signal information using a Doppler signal according to an embodiment of the present invention may be formed to include a Doppler signal acquisition step (S11), a Doppler signal processing step (S13), and a signal information output step (S15) as shown in FIG. 5.

The Doppler signal acquisition step (S11) is formed to emit a radar signal to a subject, acquire the reflected and returned radar signal to acquire a Doppler signal, and process the Doppler signal to acquire a first phase Doppler signal and a second phase Doppler signal using the Doppler signal acquisition unit.

In the case of a radar signal, when there is a motion of a subject, a Doppler signal is generated. The Doppler signal acquisition step (S11) of the present invention may be formed to emit a radar signal to a subject by utilizing the characteristics of a Doppler radar and acquire a Doppler signal through a reflected and returned signal. To this end, the Doppler signal acquisition step (S11) according to an embodiment of the present invention may include a radar signal emission step (S111), a Doppler signal conversion step (S113), and a Doppler signal separation step (S115), as shown in FIG. 6.

The radar signal emission step (S111) is formed to emit a radar signal to a subject, and the Doppler signal conversion step (S113) is formed to acquire a radar signal reflected and returned from the subject to acquire a Doppler signal. In an embodiment of the present invention, a Doppler signal can be acquired using a 24 GHz radar signal.

The Doppler signal separation step (S115) is formed to perform processing on the Doppler signal acquired from the Doppler signal conversion step (S113) to acquire a first phase Doppler signal and a second phase Doppler signal. Here, the first phase Doppler signal may be processed to have a phase difference of 90 degrees from the second phase Doppler signal.

The Doppler signal processing step (S13) according to an embodiment of the present invention is formed to process, when the Doppler signal acquisition step (S11) acquires a first phase Doppler signal and a second phase Doppler signal, the first phase Doppler signal and the second phase Doppler signal using the Doppler signal processing unit to acquire first signal information and second signal information, respectively. The first signal information and the second signal information may be acquired from the first phase Doppler signal and the second phase Doppler signal, respectively.

The first signal information and the second signal information acquired through the first phase Doppler signal may be defined as 1-1 signal information and 1-2 signal information, and the first signal information and the second signal information acquired through the second phase Doppler signal may be defined as 2-1 signal information and 2-2 signal information.

To this end, the Doppler signal processing step (S13) of the present invention may be formed to include a first Doppler signal processing step (S131), a second Doppler signal processing step (S133), and a third Doppler signal processing step (S135) as shown in FIG. 7. Hereinafter, although it is described that the Doppler signal processing step (S13) of the present invention uses three or more Doppler signal processing steps for convenience of explanation, the present invention is not limited thereto, and may operate using N Doppler signal processing steps set by a manager.

The first Doppler signal processing step (S131) is formed to perform first filtering and first amplification on the first phase Doppler signal and the second phase Doppler signal to acquire a 1-1 phase Doppler processed signal and a 2-1 phase Doppler processed signal.

The first Doppler signal processing step (S131) is formed to perform processing on the first phase Doppler signal and the second phase Doppler signal, and although it is described in the present invention that only the first Doppler signal processing step (S131) performs processing on the first and second phase Doppler signals, the present invention is not necessarily limited thereto, and as shown in FIG. 7, a 1-1 Doppler signal processing module for processing the first phase Doppler signal and a 1-2 Doppler signal processing module for processing the second phase Doppler signal may be provided.

The first filtering performed in the first Doppler signal processing step (S131) may be a process of performing low-pass filtering (LPF) by applying a filter of a frequency band set by the manager. In addition, the first amplification performed in the first Doppler signal processing step (S131) may be a process of amplifying the input first and second phase Doppler signals as much as an amplification factor set by the manager. At the first Doppler signal processing step (S131) according to an embodiment of the present invention, the Doppler signal may be processed using an active filter, and here, the active filter may be a filter that performs amplification and filtering simultaneously by utilizing circuit characteristics.

When the 1-1 phase Doppler processed signal and the 2-1 phase Doppler processed signal are generated through the first filtering and the first amplification, the generated 1-1 phase Doppler processed signal and 2-1 phase Doppler processed signal are transmitted to the second Doppler signal processing step (S133) and the third Doppler signal processing step (S135) through a branch circuit. The second Doppler signal processing step (S133) and the third Doppler signal processing step (S135) are performed using the second Doppler signal processing module and the third Doppler signal processing module connected in parallel, and although both the second Doppler signal processing step (S133) and the third Doppler signal processing step (S135) process the 1-1 phase Doppler processed signal and the 2-1 phase Doppler processed signal, the two steps are formed to perform different processing.

Describing more specifically, the second Doppler signal processing module 12B and the third Doppler signal processing module 12C are connected to the first Doppler signal processing module 12A, and the second Doppler signal processing module 12B and the third Doppler signal processing module 12C may be connected to each other in a parallel structure.

This is since that in an embodiment of the present invention, the second Doppler signal processing module 12B and the third Doppler signal processing module 12C are formed to process a signal lower than a preset frequency or a signal higher than a preset reference frequency, respectively. In an embodiment of the present invention, the third Doppler signal processing module 12C may be formed to process, when the second Doppler signal processing module 12B is formed to process a signal lower than a preset frequency, a signal higher than the preset frequency. This simply means that different frequency bands are processed through different Doppler signal processing modules, and the second Doppler signal processing module and the third Doppler signal processing module may process opposite frequency bands.

In addition, as such a parallel structure is applied, the second Doppler signal processing module and the third Doppler signal processing module may have different amplification ratios in an embodiment of the present invention, and to this end, the second Doppler signal processing module and the third Doppler signal processing module may be formed to further connect an additional Doppler signal processing module. In the present invention, a fourth Doppler signal processing module described below may be the additional Doppler signal processing module described above.

The second Doppler signal processing step (S133) is formed to perform second filtering and second amplification on the 1-1 phase Doppler processed signal and the 2-1 phase Doppler processed signal to acquire the 1-1 signal information and the 2-1 signal information.

The second Doppler signal processing step (S133) is formed to perform processing on the 1-1 phase Doppler processed signal and the 2-1 phase Doppler processed signal, and although it is described in the present invention that only the second Doppler signal processing step (S133) performs processing on the 1-1 and 2-1 phase Doppler processed signals, the present invention is not necessarily limited thereto, and as shown in FIG. 7, a 2-1 Doppler signal processing module for processing the 1-1 phase Doppler signal and a 2-2 Doppler signal processing module for processing the 2-1 phase Doppler signal may be provided.

The second filtering performed in the second Doppler signal processing step (S133) may be a process of removing DC components from the 1-1 phase Doppler processed signal and the 2-1 phase Doppler processed signal, and performing high-pass filtering (HPF) by applying a filter of a frequency band set by the manager.

In addition, the second amplification performed at the second Doppler signal processing step (S133) may be a process of amplifying the input 1-1 phase Doppler processed signal and 2-2 phase Doppler processed signal as much as an amplification factor set by the manager. An active filter may be used at the second Doppler signal processing step (S133) according to an embodiment of the present invention, and the active filter is a filter that performs amplification and filtering simultaneously by utilizing circuit characteristics.

The third Doppler signal processing step (S135) is formed to acquire the 1-1 phase Doppler processed signal and the 2-1 phase Doppler processed signal, which are the same signals as those processed at the second Doppler signal processing step (S133), and perform third filtering and third amplification on the acquired 1-1 phase Doppler processed signal and 2-1 phase Doppler processed signal to acquire 1-2 signal information and 2-2 signal information.

The third Doppler signal processing step (S135) is formed to perform processing on the 1-1 phase Doppler processed signal and the 2-1 phase Doppler processed signal, and although it is described in the present invention that only the third Doppler signal processing step (S135) performs processing on the 1-1 and 2-1 phase Doppler processed signals, the present invention is not necessarily limited thereto, and as shown in FIG. 7, a 3-1 Doppler signal processing module for processing the 1-1 phase Doppler signal and a 3-2 Doppler signal processing module for processing the 2-1 phase Doppler signal may be provided.

The third filtering performed at the third Doppler signal processing step (S135) may be a process of performing low-pass filtering (LPF) and high-pass filtering (HPF) by applying a filter of a frequency band range set by the manager. In addition, the third amplification performed at the third Doppler signal processing step (S135) may be a process of amplifying the input 1-1 and 2-1 phase Doppler processed signals as much as an amplification factor set by the manager. An active filter may be used at the third Doppler signal processing step (S135) according to an embodiment of the present invention, and the active filter is a filter that performs amplification and filtering simultaneously by utilizing circuit characteristics.

Meanwhile, in another embodiment of the present invention, a fourth Doppler signal processing step (S137) may be further included as shown in FIG. 7. The fourth Doppler signal processing step (S137) may be formed to perform processing on the processing result of the second Doppler signal processing step (S135). At this point, when the fourth Doppler signal processing step (S137) exists, the first Doppler signal processing step (S131), the second Doppler signal processing step (S133), and the fourth Doppler signal processing step (S137) may be connected in series. In addition, the signal output from the second Doppler signal processing step (S133) may be a 1-2 phase Doppler processed signal and a 2-2 phase Doppler processed signal, rather than the 1-1 signal information and the 2-1 signal information.

The fourth Doppler signal processing step (S137) is formed to perform, when the 1-2 phase Doppler processed signal and the 2-2 phase Doppler processed signal are acquired at the second Doppler signal processing step (S133), fourth filtering and fourth amplification on the 1-2 phase Doppler processed signal and the 2-2 phase Doppler processed signal to acquire the 1-1 signal information and the 2-1 signal information.

The fourth Doppler signal processing step (S137) is formed to perform processing on the 1-2 phase Doppler processed signal and the 2-2 phase Doppler processed signal, and although it is described in the present invention that only the fourth Doppler signal processing step (S137) performs processing on the 1-2 and 2-2 phase Doppler processed signals, the present invention is not necessarily limited thereto, and as shown in FIG. 7, a 4-1 Doppler signal processing module for processing the 1-2 phase Doppler signal and a 4-2 Doppler signal processing module for processing the 2-2 phase Doppler signal may be provided.

The fourth filtering performed at the fourth Doppler signal processing step (S137) may be a process of applying low-pass filtering (LPF) to the 1-2 phase Doppler processed signal and the 2-2 phase Doppler processed signal by applying a filter of a frequency band range set by the manager, and the fourth amplification may be a process of amplifying the input 1-2 phase Doppler processed signal and 2-2 phase Doppler processed signal as much as an amplification factor set in advance by the manager.

An active filter may be used at the fourth Doppler signal processing step (S137) according to an embodiment of the present invention, and the active filter is a filter that performs amplification and filtering simultaneously by utilizing circuit characteristics.

In addition, the fourth Doppler signal processing step (S137) may be formed to apply a DC offset voltage set by the manager to a signal on which the third filtering and second amplification are performed.

In an embodiment of the present invention, the 1-1 signal information and the 2-1 signal information may be information including biological motion information, and the 1-2 signal information and the 2-2 signal information may be information including movement motion information.

Accordingly, the signal information output step (S15) according to an embodiment of the present invention is formed to acquire first signal information and second signal information using a signal information output unit, and analyze the first signal information and the second signal information using a preset algorithm to acquire biometric signal information and motion signal information.

The signal information output step (S15) of the present invention may acquire 1-1 signal information and 2-1 signal information as the first signal information, and 1-2 signal information and 2-2 signal information as the second signal information. That is, in the present invention, the first signal information may be defined to include biological motion information, and the second signal information may be defined to include movement motion information.

The signal information output step (S15) may be formed to apply the acquired biological motion information and movement motion information to a preset algorithm to acquire and output biometric signal information and motion signal information from each motion information.

3. Server 20

The server may receive biometric signal information and motion signal information from the communication unit 14.

The server 20 may extract heart rate information and respiratory rate information of the subject from the received biometric signal information.

In addition, the server 20 may extract the moving speed of the subject and the area of the movement subject from the motion signal information.

The biometric signal and motion signal information acquisition device 10 using a Doppler signal may be installed in several locations within a single household. Preferably, the biometric signal and motion signal information acquisition device 10 using a Doppler signal may be installed in a bedroom, living room, small room, entrance, restroom, and the like within a single household.

Here, the biometric signal information may be heart rate and/or respiratory rate information.

In addition, the motion signal information may be the moving speed of the subject and/or the area of the movement subject.

The server 20 may acquire life pattern information by statistically calculating the time of staying in each space on the basis of the motion signal information transmitted from the biometric signal and motion signal information acquisition device 10 installed in each space of a household. For example, the server 20 may receive motion signal information from each biometric signal and motion signal information acquisition device 10 installed in a bedroom, living room, small room, restroom, entrance, and the like, and generate life pattern information by statistically calculating the time of staying in each bedroom, living room, small room, restroom, and entrance on the basis of the motion signal information.

The life pattern information generated in this way varies according to the lifestyle of each individual, and an emergency situation can be predicted on the basis of the life pattern.

Preferably, the server 20 may set a first living space, a second living space, a first danger space, and a second danger space on the basis of the life pattern information.

The first living space is a space where the subject stays the longest and may be a bedroom or a living room.

The second living space refers to a space that is neither the first danger space nor the second danger space, where the subject stays for a shorter period of time than in the first living space. For example, the second living space may be a small room.

The first danger space may be a restroom or a bathroom, which a space where the time of staying therein is shorter than in the first living space, and fall accidents occur most frequently in statistics, while it is difficult to see from the outside.

The second danger space may be an entrance that is easy to see from the outside, although the time of staying therein is shorter than in the first living space and the first danger space, and fall accidents occur frequently.

The server 20 may generate a first emergency situation signal or a second emergency situation signal when the time of staying in the first danger space or the second danger space is longer than a preset range compared to the life pattern information. In this case, the times set in advance for the first danger space and the second danger space may be different.

For example, according to the life pattern information, in the case where the time that the subject stays in the first danger space in the first time zone is n minutes, a first alarm signal may be generated when 5n minutes have passed. For example, when the average time that the subject stays in the restroom between 9:00 and 12:00 is 5 minutes, a first alarm signal may be generated when the subject stays in the restroom for 25 minutes or more. In addition, the server 20 may generate a first alarm signal when the subject stays in the restroom for 100 minutes when the average time that the subject stays in the bathroom between 17:00 and 20:00 is 20 minutes.

In addition, the server 20 may generate a second alarm signal when the time of staying in the second danger space is longer than a preset range compared to the life pattern information. For example, when the time of staying of the subject in the second danger space is n minutes according to the life pattern information, the server 20 may generate a second alarm signal when 10n minutes have passed. For example, when the average time that the subject stays in the entrance is 2 minutes, the server 20 may generate a second alarm signal when the subject stays in the entrance for 50 minutes or more.

In addition, when the ratio of the time that the subject stays in the first living space to the time that the subject is out of the first living space exceeds a preset range, a third alarm signal may be generated. For example, when the average of the ratio of the time that the subject stays in the first living space to the time that the subject is out of the first living space in the life pattern information is 7:3, and when the ratio of the time that the subject stays in the first living space exceeds a preset range of 8 (for example, the ratio of the time that the subject stays in the first living space to the time that the subject is out of the first living space is 8.2:1.8), a third alarm signal may be generated.

When the amount of activity of the subject continuously decreases in a preset time zone, the server 20 may generate a fourth alarm signal. For example, in the case where the average amount of activity of the subject is 80 between 9:00 and 17:00 on the basis of the life pattern information, the server 20 may generate a fourth alarm signal when the average amount of activity of the subject continuously decreases to 60, 50, 30, and so on in the same time zone.

The amount of activity is based on the motion signal information, and when the moving speed of the subject in the motion signal is higher than a preset value, it is regarded that an amount of activity has occurred, or when the area of the movement subject in the motion signal exceeds a preset range, it is determined that an amount of activity has occurred.

The server 20 may determine sleeping and non-sleeping of the subject on the basis of the transmitted biometric signal information and motion signal information.

When the moving speed of the subject is higher than a preset range, the area of the movement subject is larger than a preset range, and the time during which the heart rate among the biometric signal information is higher than a preset range is longer than a preset range, the server 20 determines that the subject is in the non-sleeping state.

The server 20 may statistically derive a maximum heart rate and/or respiration rate, a minimum heart rate and/or respiration rate, and an average heart rate and/or respiration rate in the non-sleeping state on the basis of the biometric signal information.

In addition, the server 20 may statistically derive a maximum heart rate and/or respiration rate, a minimum heart rate and/or respiration rate, and an average heart rate and/or respiration rate in the sleeping state on the basis of the biometric signal.

The server 20 may determine a normal range of the heart rate and/or respiratory rate of each subject (individual) in the sleeping and non-sleeping states on the basis of the statistical data. As described above, the normal range of the health state may be different in the sleeping state and the non-sleeping state.

When a heart rate and/or respiratory rate exceeding the normal range is derived in the sleeping or non-sleeping state, the server 20 may determine that the subject is in an emergency situation and generate a fourth alarm signal.

The server 20 may receive the age, gender, exercise information, drug information, and weight information of the subject from the guardian terminal 30.

First, the server 20 determines a first heart rate range according to the age of a subject in the non-sleeping state. Here, the first heart rate range means a heart rate range according to the age of the subject, which is information known previously.

Thereafter, when the received gender information is female, the server 20 determines a second heart rate corrected to be 5 to 10% higher than the first heart rate. When the gender information is male, the server 20 determines a third heart rate corrected to be 5 to 10% lower than the first heart rate.

Thereafter, the server 20 may determine the heart rate of the subject on the basis of the exercise information received from an external terminal. The external terminal is a terminal of an exercise facility such as a health club or the like, and may transmit information on the exercise amount and exercise cycle of the subject to the server 20. Alternatively, the external terminal is a wearable terminal worn on the subject, and may transmit information on the exercise amount and exercise cycle measured by the wearable terminal to the server 20.

When it is determined that the subject exercises more than a predetermined amount of exercise within a predetermined cycle, the server 20 may determine a fourth heart rate and a fifth heart rate corrected to be 5 to 10% lower than the second heart rate and the third heart rate.

The server 20 may determine a sixth heart rate correcting the fourth heart rate and determine a seventh heart rate correcting the fifth heart rate on the basis of drug information and weight information of the subject. For example, when the subject is taking a painkiller containing caffeine, the fourth heart rate and the fifth heart rate may be corrected to be higher. At this point, the correction value may vary based on the amount of caffeine contained in the drug and the weight information.

When the sixth heart rate and/or the seventh heart rate exceeds a preset range, the server 20 may determine that an emergency situation has occurred and generate a fifth alarm signal.

When the server 20 generates the first to fifth alarm signals, it may transmit the generated first to fifth alarm signals to the guardian terminal 30.

The guardian terminal 30 is a terminal owned by a person who protects the subject, and preferably, when the subject is an elderly person living alone, the guardian terminal 30 may be a terminal owned or occupied by a family member taking care of the elderly person living alone. Alternatively, the guardian terminal 30 may be a terminal owned or occupied by a person working at a nursing center, government organization, or medical facility that cares for the subject.

The above description is merely an illustrative description of the technical spirit of the present invention, and those skilled in the art will appreciate that various modifications and variations can be made without departing from the essential characteristics of the present invention. Accordingly, the embodiments disclosed in the present invention are not intended to limit the technical spirit of the present invention but to explain it, and the scope of the technical spirit of the present invention is not limited by these embodiments. The protection scope of the present invention should be interpreted by the following claims, and all technical spirits within a scope equivalent thereto should be interpreted as being included in the scope of the rights of the present invention.

The invention claimed is:

1. A personalized alarm provision system using biometric information and motion information based on a Doppler signal, the system comprising a biometric signal and motion signal information acquisition device using the Doppler signal, a server, and a guardian terminal, wherein
the biometric signal and motion signal information acquisition device using the Doppler signal includes:
a Doppler signal acquisition unit for emitting a radar signal to a subject, acquiring a reflected and returned radar signal to acquire the Doppler signal, and processing the Doppler signal to acquire a first phase Doppler signal and a second phase Doppler signal;
a Doppler signal processing unit for processing the first phase Doppler signal and the second phase Doppler signal to acquire first signal information and second signal information, respectively; and
a signal information output unit for acquiring the first signal information and the second signal information, and analyzing the first signal information and the second signal information using a preset algorithm to acquire biometric signal information and motion signal information, wherein the server acquires life pattern information by statistically calculating a time of staying in each space of a household on the basis of the motion signal information and biometric signal information, and sets living spaces and danger spaces on the basis of the life pattern information.

2. The system according to claim 1, wherein the server acquires the life pattern information by statistically calculating the time of staying in each space on the basis of the motion signal information transmitted from the biometric signal and motion signal information acquisition device installed in each space of a household, sets a space where the subject stays the longest as a first living space, sets a restroom or a bathroom as a first danger space, sets an entrance as a second danger space, and sets a space that is neither the first danger space nor the second danger space, where the subject stays for a shorter period of time than in the first living space, as a second living space.

3. The system according to claim 2, wherein the server generates a first alarm signal when a time that the subject stays in the first danger space in a first time zone has passed 5n minutes in the case where the time that the subject stays in the first danger space in the first time zone is n minutes on the basis of the life pattern information, generates a second alarm signal when a time that the subject stays in the second danger space has passed 10n minutes in the case where the time that the subject stays in the second danger space is n minutes on the basis of the life pattern information, and generates a third alarm signal when a ratio of the time that the subject stays in the first living space exceeds 8 times a ratio of a time that the subject is out of the first living space.

4. The system according to claim 3, wherein the server generates a fourth alarm signal when an amount of activity of the subject decreases in a preset time zone, wherein when a moving speed of the subject in the motion signal is higher than a preset value or when an area of a movement subject exceeds a preset range, the server determines that the amount of activity has occurred on the basis of the motion signal information.

5. The system according to claim 1, wherein the server statistically derives maximum heart and respiration rates, minimum heart and respiration rates, and average heart rate and respiration rates in sleeping and non-sleeping states on the basis of the motion signal information and biometric signal information, determines a normal range of a heart rate and a respiratory rate of the subject in the sleeping and non-sleeping states on the basis of the statistical maximum heart and respiratory rates, minimum heart and respiratory rates, average heart and respiratory rates in the sleeping and non-sleeping states, and generates a fourth alarm signal when a heart rate and a respiratory rate exceeding the normal range are derived in the sleeping or non-sleeping state.

6. The system according to claim 1, further comprising an external terminal that transmits exercise information of the subject, wherein the server receives an age, a gender, exercise information, drug information, and weight information of the subject from the guardian terminal, determines a first heart rate range according to the age of the subject in the non-sleeping state, then, determines a second heart rate corrected to be 5 to 10% higher than the first heart rate when the gender of the subject is female, and determines a third heart rate corrected to be 5 to 10% lower than the first heart rate when the gender of the subject is male, then, determines a fourth heart rate corrected to be 5 to 10% lower than the second heart rate and a fifth heart rate corrected to be 5 to 10% lower than the third heart rate when it is determined that the subject exercises more than a predetermined amount of exercise within a predetermined cycle on the basis of the exercise information received from the external terminal, then, determines a sixth heart rate correcting the fourth heart rate, and determines a seventh heart rate correcting the fifth heart rate on the basis of the drug information and weight information of the subject, and determines that an emergency situation has occurred, and generates a fifth alarm signal when the sixth heart rate and the seventh heart rate exceed a preset range.

* * * * *